United States Patent
Salman et al.

(10) Patent No.: US 6,441,226 B1
(45) Date of Patent: Aug. 27, 2002

(54) PROCESS FOR THE PREPARATION OF ISOTRETINOIN

(75) Inventors: Mohammad Salman, Gurgaon; Vijay Kumar Kaul, New Delhi; J. Suresh Babu; Naresh Kumar, both of Gurgaon, all of (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/467,201

(22) Filed: Dec. 20, 1999

(30) Foreign Application Priority Data

Jul. 30, 1999 (IN) ........................ 1037/DEL/99

(51) Int. Cl.[7] .............................. C07C 61/16

(52) U.S. Cl. ...................................... 562/510

(58) Field of Search ........................ 562/510

(56) References Cited

U.S. PATENT DOCUMENTS

| | | | |
|---|---|---|---|
| 4,556,518 A | | 12/1985 | Lucci et al. |
| 4,677,120 A | * | 6/1987 | Parish et al. |
| 4,916,250 A | | 4/1990 | Babler et al. |
| 4,966,965 A | * | 10/1990 | DeLuca et al. |
| 5,191,110 A | * | 3/1993 | Solladie et al. |
| 5,424,465 A | * | 6/1995 | John et al. |
| 5,892,073 A | * | 4/1999 | Magnone |
| 5,925,797 A | * | 7/1999 | Giraud et al. |

FOREIGN PATENT DOCUMENTS

GB          835 526 A     5/1960

OTHER PUBLICATIONS

C.F. Garbers, D.F. Schneider, and J.P. Van Der Merwe, Synthesis of cis–2, cis–4–Vitamin A Acid by a Wittig Condensation, 1968, Journal of Chemical Society, 1982–1983.

Gerald Pattenden and B.C.L. Weedon, Carotenoids and Related Compounds Part XVIII. Synthesis of cis–and Di–cis–Polyenes by Reactions of the Wittig Type, 1968, Journal of Chemical Society, 1984–1997.

Guy Solladie and Andre' Girardin, Synthesis of New Aromatic Retinoid Analogues by Low–Valent Titanium Induced Reductive Elimination, 1989, Journal of Orgainic Chemistry, 54, 2620–2628.

Dugger, R.W., A General Synthesis of 5,6–dihydro–.alpha.–pyrones, Journal of Organic Chemistry, 1980, 45(7), 1181–5.XP002152898.

Gianfranco Cainelli, Some Aspects of the stereospecific synthesis of terpenoids by means of isoprene units, Acc. Chem. Res., 1981, 14(3), 89–94, XP002152900.

Chemical Abstracts, vol. 79, No. 9, Sep. 3, 1973, Abstract No. 53630.

Gianfranco Cainelli, Synthesis of compounds containing the isoprene unit, New Synthesis of Vitamin A, Gazz. Chim. Ital., 1973, 103(1–2), 117–25. XP002152901.

U.Schwieter, C.V. Planta, R. Ruegg and O. Isler, 63. Suntheses in the Vitamin A2 Series, 2nd Notification, The Representation of Four Sterically Unhindered vitamin A2 Isomers, 1962, 45, 517, XP–002152899,(Translated into English from German).

* cited by examiner

Primary Examiner—Paul J. Killos
(74) Attorney, Agent, or Firm—Jayadeep R. Deshmukh, Esq.

(57) ABSTRACT

The present invention relates to a process for the preparation of 13-cis isomer of Vitamin A acid, commonly known as isotretinoin, in a single step.

9 Claims, No Drawings

PROCESS FOR THE PREPARATION OF ISOTRETINOIN

FIELD OF THE INVENTION

The present invention relates to a process for the preparation of 13-cis isomer of Vitamin A acid, commonly known as isotretinoin, in a single step.

BACKGROUND OF THE INVENTION

Isotretinoin (13-cis retinoic acid) belongs to a family of Vitamin A (retinol) related compounds. It inhibits sebaceous gland function and keratinization and is used for the treatment of dermatological diseases like acne. It is extremely effective in very severe and nodulocystic acne and prevents scarring. More recently, isotretinoin has also been evaluated for its potential use in certain cancerous conditions.

Structurally, isotretinoin is a highly conjugated molecule consisting of a substituted cyclohexene moiety and a nine-carbon polyene side chain with a terminal carboxy group. All but one of the double bonds (C-13 double bond) in the side chain are trans and it is the stereospecific construction of this polyene side chain which has challenged synthetic organic chemist for the last almost three decades. Commercially and readily available β-ionone has been conveniently used for the construction of the cyclohexene part of isotretinoin. The synthetic prior art approaches for the construction of the polyene side chain are summarized below.

In general, a convergent approach, involving stereospecific coupling of the appropriate $C_{15}$ (synthesized from β-ionone) and $C_5$ synthons, has been utilized. (however, a linear sequence comprising of seven steps, starting from β-ionone, has also been described; J Org. Chem. 54, 2620–2628, 1989). For example, Patternden and Weedon, J. Chem. Soc.(C), 1984–97 (1968) have disclosed a procedure for the preparation of 13-cis retinoic acid by reacting a $C_{15}$-triarylphosphonium salt (Wittig salt) and a $C_5$-butenolide in diethylether to produce an isomeric mixture (of the cis and trans isomers at C-11 double bond) of 13-cis retinoic acid in 66–75% yield; the desired 11-trans-13-cis content is only about 36% and the rest being the corresponding 11,13-di cis isomer. Selective isomerization of the 11-cis double bond in the presence of 13-cis double bond proved extremely difficult to accomplish. A great deal of effort has been directed to affect selective isomerization of 11-cis double bond (without isomerizing the 13-cis double bond) in 11,13-di cis retinoic acid. The methods include photoisomerisation by using either iodine (J. Chem. Soc. (C) 1982, 1968), transition metal catalysts (U.S. Pat. No. 4,556,518) or photosensitizers such as erythrosin B, rose Bengal etc. (U.S. Pat. No. 5,424,465). These processes suffer from the following limitations and for various reasons are not suitable for commercial production of isotretinoin. For example, the process for selective photoisomerization using iodine under diffused light is extremely difficult to accomplish without affecting the 13-cis double bond. This results in the generation of all trans retinoic acid (tretinoin) as a major impurity in isotretinoin produced by this process. Although, U.S. Pat. No. 5,424,465 describe that use of photosensitizers enhances selectivity of photoisomerisation of $C_{11}$-cis double bond, no data, however, is provided for the extent of tretinoin formation in this process.

The use of the palladium catalysts, as described in U.S. Pat. No. 4,556,518, could potentially lead to the contamination of the desired isotretinoin with traces of transition metals and thereby might lead to problems with the stability. In addition, the process involves an elaborate extraction procedure for the work-up.

U.S. Pat. No. 4,916,250 describes a process involving use of a phosphonate ester (as a $C_{15}$ synthon), which is first generated in several steps starting from β-ionone. The phosphonate ester is then reacted with 5-hydroxy-4-methyl-2- (5H)-furanone ($C_5$ synthon) to afford isotretinoin. Although this approach does not involve the cumbersome photoisomerization step, it is uneconomical at a commercial manufacturing scale because of the large number of steps.

Cainelli et al, Gazz. Chim. Ital, 103, 117–125 (1973) reported the synthesis of isotretinoin by reacting a dienolate of sodium 3,3-dimethyl acrylate ($C_5$-synthon) with β-ionylideneacetaldeyhyde ($C_{15}$ synthons) at −78° C. for twelve hours to give a hydroxy acid intermediate. The hydroxy acid intermediate on conversion to intermediate lactone and subsequent treatment with base afforded isotretinoin. This approach suffers from the following limitations two different bases (sodium hydride and lithium diisopropylamide) are required and moreover generation of dienolate requires maintaining low temperatures (−78° C.) for extended periods of time, which would entail very high energy costs at the commercial scale. Furthermore, the purification of the intermediate lactone by preparative High Performance Liquid Chromatography, as suggested, is not commercially feasible.

SUMMARY OF THE INVENTION

It is an object of the present invention to solve the problems associated with the prior art and to provide an efficient method for the synthesis of isotretinoin of high purity in one single step (stereospecific coupling of $C_{15}$ and $C_5$ synthons) using conditions which are convenient to operate on a commercial scale.

It is a further object of the present invention to provide a process which affords isotretinoin while controlling the levels of tretinoin to <0.1%. Various pharmacopoeias have prescribed a 1–2% limit of this impurity in isotretinoin.

The present invention is directed to a process for the preparation of isotretinoin, which comprises the condensation of dienolate of methyl-3,3-dimethylacrylate of Formula I:

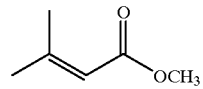

with β-ionylideneacetaldehyde of Formula II:

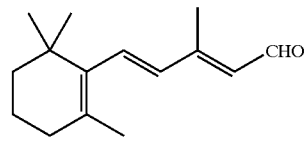

in a suitable solvent at (I) −60° C. to −80° C. for 1–2 hours and (ii) 25° C.–45° C. for 1–24 hours, followed by aqueous acidic work up to give isotretinoin in a single step.

The condensation reaction proceeds via the formation of the intermediate lactone of Formula III:

III

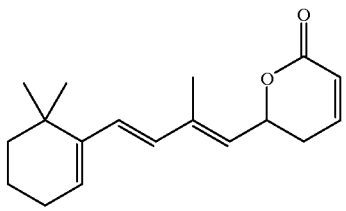

which is not isolated. Lactonization results in the release of a methoxide ion which in turn opens the lactone to afford isotretinoin (as carboxylate salt); the reaction of methoxide and lactone is facilitated by higher temperatures (25–45° C.) and by carrying the reaction for longer time. Aqueous acidic work up thus produces isotretinoin in one single step starting from β-ionylidene acetaldehyde.

Generally, the initial condensation of dienolate of methyl-3,3-dimethyl acrylate of Formula I shown above with β-ionylidene-acetaldehyde of Formula-II above is carried out at −60° C. to −80° C. for 1–2 hours. Preferably, it is carried out at −65° C. to −75° C. Temperature is later raised to about 25° C.–45° C., preferably between 30–40° C. and is maintained for 1–24 hours and the progress of the reaction is monitored. Suitable solvents include tetrahydrofuran, 1,4-dioxane, hexanes, diisopropyl ether, hexamethyl-phosphoramide, tetramethylurea, and mixtures thereof. Tetrahydrofuran is a preferred solvent.

Aqueous acidic work up involves the adjustment of pH with mineral acids and extraction with organic solvents. Acids may include hydrochloric acid, sulfuric acid, and phosphoric acid. Sulfuric acid being the preferred acid. Any organic solvent may be used for extraction and such solvents are known to a person of ordinary skill in the art and include: water-immiscible solvents, such as chloroform, dichloromethane, 1,2-dichloroethane, hexane, toluene, ethyl acetate and the like.

Other features of the invention will become apparent in the course of the following description of exemplary embodiment, which is given for illustration of the invention, and are not intended to be limiting thereof.

DETAILED DESCRIPTION OF THE INVENTION

EXAMPLE 1

Under an atmosphere of nitrogen, a solution of n-butyl lithium in hexane (321 ml, 15%) was added to a solution of diisopropylamine (48.6 g, 0.48 mole) in tetrahydrofuran (1000 ml) at −30° C. and the mixture was stirred for one hour. The reaction mixture was then cooled to −72° C. and methyl 3,3-dimethyl acrylate (55 g, 0.48 mole) was added to it. Stirring was continued at −65 to −75° C. for 30 minutes. To the resulting mixture, a solution of β-ionylidene acetaldehyde (100 g, 0.458 mole, 9-trans content: 80%) was added and the reaction mixture was stirred at −65 to −75° C. for one hour. The reaction mixture was then warmed to 40° C. and stirred at this temperature for three hours. Solvent was removed under vacuum and the reaction mixture was diluted with water (700 ml) and methanol (300 ml). Activated charcoal (4 g) was then added and the mixture was refluxed for 30 minutes. The heterogeneous mixture was filtered through hyflo and the hyflo bed was washed with methanol (300 ml) and water (150 ml). The aqueous methanolic layer was then extracted with hexanes (2×500 ml) and acidified with 10% sulfuric acid to pH 2.8±0.5. The desired product was then extracted with dichloromethane (2×500 ml). The combined dichloromethane layer was washed with water (2×300 ml) and concentrated in vacuo to afford the desired isotretinoin. Crystallization from methanol (200 ml) afforded isotretinoin (44 g) in greater than 99% HPLC purity; the tretinoin content was less than 0.1% by HPLC.

EXAMPLE 2

Under an atmosphere of nitrogen, a solution of n-butyl lithium in hexane (20 ml, 15%) was added to a solution of diisopropylamine (2.7 g, 0.027 mole) in diisopropyl ether (10 ml) at −74° C. and the reaction mixture stirred for 0.5 hour. To this, methyl 3,3-dimethyl acrylate (2.51 g, 0.022 mole) was added at −74° C. Stirring was continued at −70° C.±2° for 30 minutes and the reaction mixture was added to a solution of β-ionylidene acetaldehyde (5 g, 0.022 mole, 9-trans content: 80%) in diisopropyl ether (20 ml) at −74° C. The reaction mixture was stirred for 1 hour at −72° C.±2° and then slowly allowed to warm to room temperature. The reaction mixture was stirred at ambient temperature overnight and worked up as per the procedure given in example 1 to afford 1.03 g of pure isotretinoin.

While the present invention has been described in terms of its specific embodiments, certain modifications and equivalents will be apparent to those skilled in the art and are intended to be included within the scope of the present invention.

We claim:
1. A process for the preparation of isotretinoin in a single step, which comprises:

condensation of dienolate of methyl 3,3-dimethyl acrylate of Formula I:

I

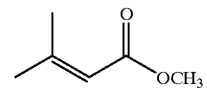

with β-ionylidene-acetaldehyde of Formula II:

II

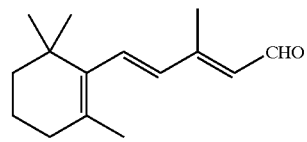

in a suitable solvent at a temperature between −60° C. to −80° C. for 1–2 hours to produce the intermediate lactone of Formula III, and

III

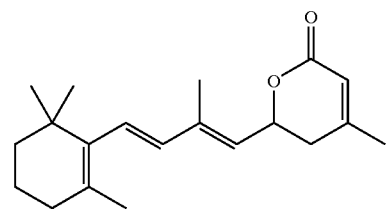

raising temperature of the reaction mixture to 25° C. to 45° C. and stirring for 1–24 hours;
followed by aqueous acidic work up to form isotretinoin of Formula IV:

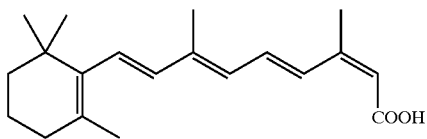

containing less than 0.1% of tretinoin impurity of Formula V:

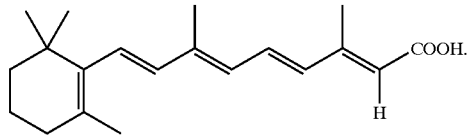

2. The process of claim 1, wherein said solvent is selected from the group consisting of tetrahydrofuran, 1,4-dioxane, hexanes, diisopropyl ether, hexamethyl-phosphoramide, tetramethyl urea, and mixtures thereof.

3. The process of claim 2 wherein said solvent is tetrahydrofuran.

4. The process of claim 1 wherein said aqueous acidic work up is done in the presence of water and a mineral acid.

5. The process of claim 4 wherein mineral acid is selected from hydrochloric acid, sulfuric acid, and phosphoric acid.

6. The process of claim 1 wherein said aqueous acidic work up includes extraction with an organic solvent.

7. The process of claim 6 wherein organic solvent is water-immiscible.

8. The process of claim 7 wherein organic solvent is selected from chloroform, dichloromethane, 1,2-dichloroethane, hexane, toluene, and ethyl acetate.

9. The process of claim 1 wherein an intermediate lactone of formula III:

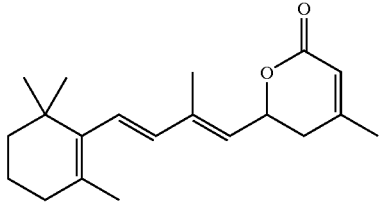

is produced in situ.

* * * * *